United States Patent [19]

Huetsch et al.

[11] Patent Number: 5,083,864
[45] Date of Patent: Jan. 28, 1992

[54] GRAPHITE TUBE FURNACE WITH STATIONARY SPECIMEN SUPPORT FOR ATOMIC ABSORPTION SPECTOSCOPY

[75] Inventors: Bruno Huetsch; Bernd Schmidt, both of Bonn, Fed. Rep. of Germany

[73] Assignee: Ringsdorff-Werke GmbH, Bonn, Fed. Rep. of Germany

[21] Appl. No.: 656,287

[22] Filed: Feb. 14, 1991

[30] Foreign Application Priority Data

Feb. 15, 1990 [EP] European Pat. Off. ......... 90102929.8

[51] Int. Cl.[5] ............................................ G01N 21/74
[52] U.S. Cl. ...................................................... 356/312
[58] Field of Search ................................ 356/312, 244

[56] References Cited

U.S. PATENT DOCUMENTS

| | | | |
|---|---|---|---|
| 4,303,339 | 1/1981 | Gläser | 356/312 X |
| 4,946,278 | 8/1990 | Hütsch et al. | 356/312 |
| 4,971,438 | 11/1990 | Hütsch et al. | 356/312 |

FOREIGN PATENT DOCUMENTS

| | | |
|---|---|---|
| 2924123 | 4/1985 | Fed. Rep. of Germany . |
| 3545635 | 6/1987 | Fed. Rep. of Germany . |
| 3722379 | 3/1988 | Fed. Rep. of Germany . |
| 8714926 | 3/1988 | Fed. Rep. of Germany . |
| 8803144 | 6/1988 | Fed. Rep. of Germany . |
| 3823346 | 1/1990 | Fed. Rep. of Germany . |
| 2195766 | 8/1987 | United Kingdom . . |

OTHER PUBLICATIONS

Journal of Analytical Atomic Spectrometry, Mar. 1987, vol. 2, Ian L. Shuttler and H. Trevor Delves: "Between-Batch Variability of Thermal Characteristics of Commercially Available L'vov Platform Graphite Tube Atomisers, etc.", p. 171.

Lectures; Heinz Falk and Andreas Glismann: "Spatially and temporally resolved temperature profiles in graphite furnaces"; pp. 748 to 753, 1986, Fresenius Z Anal. Chem.

Primary Examiner—Vincent P. McGraw
Attorney, Agent, or Firm—Herbert L. Lerner; Laurence A. Greenberg

[57] ABSTRACT

A graphite tube furnace for atomic absorption spectroscopy has a specimen support. The graphite tube furnace is constructed with zones disposed substantially symmetrically around the center of the furnace. The shape of the zones is largely matched and matchable to the functions of the device, such as electric contacting, prevention of heat sinks, restriction of an atomization chamber, provision of an atomization chamber and holding of the specimen support. The specimen support is formed in such a way that in practice it is no longer heated by Joulean heat or thermal conduction, it is secured against movements and it has a minimal mass.

7 Claims, 5 Drawing Sheets

GRAPHITE TUBE FURNACE WITH STATIONARY SPECIMEN SUPPORT FOR ATOMIC ABSORPTION SPECTROSCOPY

The invention relates to a graphite tube furnace for atomic absorption spectroscopy, having at least two surrounding flanges disposed at a distance from the ends of the tube furnace on a circumferential line at the inner surface of the furnace wall, and a specimen support resting in flange grooves incorporated in the flanges in the furnace, the specimen support being formed of sections, having at least one recess for receiving an analysis specimen and being held essentially away from the inner surface of the wall of the tube furnace.

In atomic absorption spectroscopy, in order to obtain measurement values with a comparatively small spread, it is advantageous to heat the graphite tube furnace and the specimen support to the required temperature independently of one another and with a temporal delay in order to ensure that the vaporization and atomization of the analysis substance only take place when the temperature has been stabilized within the graphite tube furnace. Such a configuration, with which the measurement of the atomic absorption could be measured under predominantly reproducible defined conditions, has already been proposed by L'vov.

Various simplifications have been proposed as a consequence of the high expenditure for apparatus and measurement which are associated with that configuration.

With almost all such varied apparatuses, the specimen support disposed in the graphite tube furnace does not have any resistance heating circuit of its own so that specimen supports and specimens are heated by irradiation as well as by a certain amount of Joulean heat and by thermal conduction.

The reproducible adjustment of the factors determining the analysis precision, like the avoidance of temperature fluctuations over the volume of the cuvette, the residence time of the vaporized analysis substance in the cuvette, the atomization time and the ratio of the residence time to the atomization time, as well as the prevention of the occurrence of matrix effects, that is reactions of the element being investigated with other constituents of the analysis substance or of the graphite tube furnace or specimen support for compounds which are resistant in zones of lower temperature, is of great importance with such configurations, but heretofore has not been resolved to complete satisfaction.

A further problem is the secure fixing of the specimen support in the graphite tube furnace. This is especially important when working in strong magnetic fields, such as for example with the Zeeman underground compensator. As a result of the oscillations occurring therewith, the specimen support can even be displaced out of the graphite tube furnace.

In the publication Fresenius Z. Anal. Chem. (1986) 323, 748 to 753, published by Springer Verlag, H. Falk and A. Glismann make it known that the temperature difference and the heating rate of the specimen support at a constant heating rate of the graphite tube furnace, are influenced essentially by electrical contacts between tube wall and the specimen support, since a part of the furnace current flows through the plate-shaped specimen support lying on the furnace wall. The effect of different temperature differences and heating rates, e.g. in the determination of small lead contents in blood, has been investigated by I.L. Shuttler and H.T. Delves in the Journal of Analytical Atomic Spectrometry, Mar. 1987, Vol. 2, page 171. However, the variation in the measurement values was so large with standard specimen supports that the analysis method was not suitable for that determination. Above all there were significant differences in the release time of the signal and the integral absorption, which apparently goes back to differences in the heating rate of the specimen. The authors maintain that the usual specimen supports are heated not only by radiation but also by heat conduction and Joulean heat. In order to resolve the problem, there has been proposed the development of specimen supports which are heated exclusively by radiation and can be held in a reproducible position in the graphite tube furnace.

An improvement with respect to the parallelepipedic standard specimen supports having comparatively large contact surfaces with the graphite tube furnace is the "pin-platform" (loc.cit.). In order to reduce the contact surface, such a specimen support makes contact with pin-like supports on the wall surface of the furnace. However, the general use of that structural form is subject to the following disadvantages: the position of the specimen support in the graphite tube furnace is not positively set so that its precise position in the tube furnace depends on service personnel, the heating of the support by Joulean heat is not completely excluded and the pin-like supports essentially reduce the choice of materials for the specimen support since with pins, different specimen supports may only be produced with a justifiable expenditure from special types of graphite, such as for example vitreous carbon, which moreover may only be produced with difficulty in the necessary purity.

Essentially three configurations of the specimen support have become known which are distinguished by a comparatively small contact area between the tube wall and the specimen support and which significantly restrict electric conduction and thermal conduction between the wall and the support.

The structures according to German Patent DE 29 24 123 C2, corresponding to U.S. Pat. No. 4,303,339 and German Petty Patent DE G 87 14 926.5 are typical of the first group. According to German Patent DE 29 24 123 C2, corresponding to U.S. Pat. No. 4,303,339, the specimen support has a trapezoidal cross-section and lies in corresponding dove-tail or trapezoidally-shaped recesses which are incorporated in the wall of the tube furnace. However, as a result of the introduction of groove-shaped recesses into the interior of the wall of the tube furnace, positions of weakness exist which lead to early failure. The stresses occurring with pulse-like heating and cooling following thereon lead to cracks which extend from the inner edges of the grooves and make the tube furnace unusable. With the structural form according to German Petty Patent DE G 87 14 926.5, the specimen support lies in the grooves but only along one line. As a result of that solution, the heating of the specimen support by the production of Joulean heat and thermal conductivity is already strongly reduced and the mounting of the specimen support in the tube furnace is improved. The above-described weakening of the tube furnace housing by the grooves is also present in that case. The heating of the specimen support by Joulean heat is always still too high since one end of the specimen support can still maintain direct contact with the heat supply configuration of the tube furnace. Finally, the mass of the tube furnace is still too high for a rapid heating.

In the second construction, the specimen support has a peg with a small cross-sectional area which is inserted in a bore in the graphite tube and holds the specimen support away from the tubular wall (as in German Published, Non-Prosecuted Application DE 35 45 635 A1). Due to the small dimensions and the brittleness of the material graphite, a high expenditure is necessary for the production of such a specimen support. For reasons of material strength, only vitreous carbon is suitable for such usage. Disadvantages of vitreous carbon in atomic absorption spectroscopy have been indicated above. Moreover, undesired stresses and cracks on the holding elements for the specimen support also occur in that case.

Typical of the third group is a specimen support whose expanded end section engages in slots which extend from one or both end surfaces of the graphite tube. The specimen supporting part of the support is freely suspended at a distance from the tube wall (as in German Published, Non-Prosecuted Application DE 37 22 379 A1, corresponding to Published U.K. Application GB 2 195 766 A, and German Petty Patent DE G 88 03 144.6, corresponding to U.S. application Ser. No. 319,136, now U.S. Pat. No. 4,971,438. The structural form according to that group reduces the heat flow between the graphite tube and the specimen support and permits the precise establishment of the specimen position relative to the graphite tube. The atomization furnace according to German Published, Non-Prosecuted Application DE 37 22 379 A1, corresponding to Published U.K. Application GB 2 195 766 A also minimizes the production of heat electrically in the specimen support. The disadvantage of such structural forms lies in the weakening of the thermally and mechanically strongly stressed end surfaces of the tube furnace by the recesses in which the specimen supports engage. Upon rapid heating many times, damage occurs as a result of fine cracks which gives rise to a rupture of the graphite tube.

Thermal expansion coefficients of the specimen support and the tube impose additional pressure stresses on heating that can lead to the rupture of the slotted section, which is a source of damage that can also lead to failure with the structural forms according to the first and second tube furnace types. Destruction by arcing is common if the mechanical stresses are limited by too large a margin.

A further improved graphite tube furnace with a specimen support is known from German Published, Non-Prosecuted Application DE 38 23 346 A1, corresponding to U.S. Pat. No. 4,946,278. In that case the specimen support lies on surrounding flanges on the interior of the wall surface of the tube furnace, wherein the flanges have groove-shaped supports. The position of the specimen support in the horizontal is established by means of the groove-shaped recesses and an additional flange serving as abutment. The groove-shaped recesses are only incorporated in the flanges. The tube housing is not weakened by them. The undesired heating of the specimen support by thermal conduction and Joulean heat could be further reduced by the further reduction of the contact surface between specimen support and tube furnace. If the flanges are disposed symmetrically relative to the tube ends, a central furnace part is obtained in which the setting up of isothermal conditions is improved. In spite of such improvements, even that atomization furnace is still not satisfactory.

With that type of tube furnace, a strong flow of heat to the tube furnace end connected with the cooled current connectors is observed. That leads to the formation of heat sinks in the region next to the atomization zone. The flange serving as an abutment makes an additional contribution to the production of temperature imbalances. Under such conditions, matrix effects influence the analysis results disadvantageously. In addition, the specimen support is supported over an area in the recesses of the flanges and can have electrical contact with the current supply configuration at the ends of the tube furnace. As a result, the formation of sharp absorption signals is disturbed. A further disadvantage of such a configuration lies a lack of fixing the specimen support against movements at right angles to its horizontal position. However, such a fixing is necessary when working in stronger magnetic fields such as in the Zeeman underground compensator.

It is accordingly an object of the invention to provide a graphite tube furnace with a stationary specimen support for atomic absorption spectroscopy, which overcomes the hereinafore-mentioned disadvantages of the heretofore-known devices of this general type and which lies in the cost range of usual structural forms with regard to production and use.

In particular, with the solution according to the invention:
- the occurrence of heat sinks in zones near to the atomization zones is to be prevented,
- a direct contacting of the specimen support with the current supply at the ends of the tube furnace is to be rendered impossible,
- the heating of the specimen support by electrical current and thermal conduction is to be further reduced,
- a rapid reproducible atomization of the analysis specimen and predominantly isothermal conditions is to be guaranteed, and
- the specimen support is to be secured against movements in all directions.

With the foregoing and other objects in view there is provided, in accordance with the invention, a graphite tube furnace assembly for atomic absorption spectroscopy, comprising a graphite tube furnace having a longitudinal axis, an opening, ends, and a wall with an inner surface, and an interior with a central region, the interior of the tube furnace having the following sequentially disposed zones as seen from one of the ends: a first starting zone with a first inner diameter and an inner section, a second zone with a second inner diameter being larger than the first inner diameter, a third zone with a third inner diameter being smaller than the first inner diameter, the third zone having a lateral edge facing the second zone and at least one surrounding flange formed at a distance from the ends along a circumferential line on the inner surface, the surrounding flange having two groove-shaped supports formed therein, a fourth zone forming the central region and having a fourth inner diameter being greater than the third inner diameter and less than the first inner diameter, a fifth zone having a fifth inner diameter corresponding to the third inner diameter and at least one other surrounding flange formed at a distance from the ends along a circumferential line on the inner surface, the other surrounding flange having another groove-shaped support formed therein, a sixth zone having a sixth inner diameter corresponding to the second inner diameter, and a seventh zone having a seventh inner diameter corresponding to the first inner diameter; and a specimen support to be inserted in the tube furnace and held in the groove-shaped supports essentially at a distance from the inner surface, the specimen support having at least one relatively wider end section facing one of the ends of the tube furnace and one relatively narrower section adjoining the at least one wider end section and being disposed in the central region, after insertion of the specimen support in the tube furnace, the at least one wider end section having a shape cooperating with the inner section of the first starting zone and the lateral edge of the third zone of the tube furnace for preventing the specimen support from moving parallel to the longitudinal axis of the tube furnace after pushing of the specimen support into the groove-shaped supports, the narrower section having at least one recess formed therein for receiving an analysis specimen, and the specimen support having an end facing the opening of the tube furnace and being disposed at a distance from one of the ends of the tube furnace.

The division of the interior space of the tube furnace into zones achieves several aims. The first zone I has a wall thickness which is suitable for contacting with the current supply configuration. The second zone II has the smallest wall thickness and accordingly cross-sectional area of all of the zones. As a result, too strong a heat outflow from the middle part of the tube furnace to the ends and accordingly the occurrence of heat sinks is prevented. The increased development of Joulean heat in these zones of small cross-section is advantageous and reinforces the desired effect, and matrix effects are accordingly minimized. The section at the transition from the first zone I to the second zone II serves as an abutment for the wider part of the specimen support. As a result, the specimen support is limited in its movement to the end of the tube furnace and there is prevention of contact with the current supply configuration.

The third zone III following the second zone II, which is the same as the fifth zone V, is formed of a flange running around a circumferential line of the interior of the tube. The flanges of the third zone III and the fifth zone V enclose the atomization zone and form a barrier for preventing the outflow of a gas cloud containing the atomized substance and thus increase the residence time of the analysis substance in the measuring cell and accordingly the precision of analysis.

In accordance with another feature of the invention, two trapezoidal grooves are moreover incorporated in each of the flanges of the third zone III and the fifth zone V on a plane below the plane of a horizontal section through the longitudinal axis of the tube, and the likewise trapezoidal specimen support whose greatest width has a larger dimension than the connection line between the two oppositely disposed surfaces of the flanges at the positions at which the trapezoidal grooves or notches begin and where the grooves or notches have their greatest depth, is pushed into these grooves. As a result of this configuration, the specimen support is prevented from experiencing vertical movements and cannot be displaced by strong vibrations or shaking upwardly out of its position. The lateral edges of the flanges of the third zone III facing the tube opening simultaneously serve as abutments for the wider part of the specimen support, as a result they limit the longitudinal motion of the specimen support in the direction of the interior of the tube and secure it together with the abutment at the inner surface of the first zone I in its position in the tube furnace with respect to each movement along the longitudinal axis of the furnace. The preferred form of the flanges is that of a truncated pyramid with a width at the foot of 2 mm and at the top of 1 mm and a height, as measured from the plane of the fourth zone IV of 0.4 mm. However, the invention is not limited to this form and these dimensions. They can be matched to the respective situations on each occasion. It is also not necessary for the third flange zone III to follow the second zone II directly. For reasons of adjustment of the temperature conditions at the second zone II, due to the setting of a specific tube length or for stability reasons, a further zone having an inner diameter which may not be less than that of the first zone I, can additionally be disposed between the second and third zones II and III. It conveniently has the same inner diameter as the first zone I.

Following the third zone III is zone the fourth IV which is delimited on the other side by the flange of the fifth zone V and which encloses the analysis specimen containing part of the specimen support. In this zone, the substance to be analyzed is vaporized and atomized by thermal radiation emitted by the furnace walls. The gas cloud being produced is kept in the zone for a certain time during which the spectral analytical procedure occurs, with the two bounding flanges acting supportingly. In order to ensure that no heat sink occurs at the ends of the tube furnace and that a delayed heating up of the analysis specimen takes place, this zone has the greatest wall thickness, that is the smallest inner diameter.

Following the fourth zone IV is the fifth zone V which is formed just like the third zone III. The sixth zone VI following the fifth zone V has the same wall thickness as the second zone II and also fulfils the same purpose. In this case as well, a further zone can be placed between fifth zone V and the sixth zone VI, which is like the further zone placed between the second zone II and the third zone III and is similar to the zone lying between the second zone II and zone the third III or corresponds thereto.

The second end of the tube is formed by the seventh zone VII whose diameter and formation corresponds to first zone I. It serves for the electrical contacting at the other end of the tube furnace.

A symmetrical construction is especially advantageous for the operation of the graphite tube furnace. The first and seventh zones I and VII, and the second and sixth zones II and VI which correspond to each other, possibly the two intermediate zones which then follow, as well as the third and fifth zones III and V, in this case have the same form and the same distance from the center of the tube for each zone pair, with the center of the fourth zone IV corresponding to the center of the tube furnace. This structural form largely guarantees that the course of an analysis will proceed completely in the desired type and manner and that disturbances such as premature vaporization of the analysis specimen, temperature inhomogenities in the analysis chamber (fourth zone IV), temperature sinks in the direction of the ends of the furnace, and matrix effects are reduced to an extent which can be ignored. Deviations from a rigorously symmetrical structure then become necessary if matching to special operative or process technique situations make this necessary. The tube furnace construction offers sufficient possibilities for this purpose. Thus, e.g. by changing the size of the second zone II and, should this be advantageous, by changes in connection with the intermediate zone lying between the second and third zones II and III, the temperature profile in the furnace can be displaced temporally and spatially.

The specimen support is formed of at least two sections that are connected together, in the form of a first wider one facing the end of the tube furnace and a second narrower one which begins at the third zone III and ends at the fifth zone V. It is formed in such a way that it has as small a mass as possible with sufficient stability during use and is structurally formed in such a way that, after introduction into the tube furnace, it is secured against displacement in all three directions of the chamber as well as being held at a distance from the inner wall surface of the tube furnace.

The first section is essentially formed of two webs which extend from the second section and which run in a symmetrical configuration at a distance from the furnace wall with the specimen support inserted in the tube furnace. The total width of the first part is chosen in such a way that the webs are held away from the inner wall surface of the second tube furnace zone II and optionally the zone between the second and third zones II and III, but bump against the surrounding flange of the third zone III.

In accordance with a further feature of the invention, disposed at the side of the end of the tube furnace, on both ends of the webs or legs, are cantilevers which are mounted in such a way that upon pushing the specimen support into the tube furnace they abut the outer edge of the first zone I and can only be pushed by slight bending of the webs or legs over this zone and immediately spring back behind again into their starting position. The cantilevers then lie on the section of the first zone I facing the interior of the tube furnace, they prevent movement of the specimen support in the direction of the first zone I out of its position and therefore hold the specimen support away from the electric contacting configuration. In order to minimize the mass of this part of the specimen support, the webs or legs have just sufficient material thickness for its mechanical stability. The lateral edges of the limbs facing the inner walls of the furnace are sloped for maintaining the necessary distancing.

The second internal part of the specimen support relative to its position in the tube furnace has a trapezoidally-shaped cross-section and is provided with a recess for receiving the analysis specimen. It is pushed horizontally into the grooves of third and fifth zones III and V up to the abutment of the inner shoulder of the first part of the specimen support at the flange of third zone III and as is explained above it is then secured against movements in three directions of the chamber. The two acute angles of the trapezium of the specimen support and at the grooves of the third and fifth zones III and V are different in order to ensure that the specimen support is only supported in the grooves along one line and otherwise is held away from the wall of the tube furnace. As a result of this structural form, electrical current transport and heat conduction are loaded from the graphite tube furnace on to the specimen support to a negligible extent. The placement of a plate-shaped specimen support in trapezoidal grooves of a graphite tube furnace with non-parallel surfaces of the grooves of the specimen support and the grooves of the graphite tube furnace making contact, is the subject of the invention of German Petty Patent DE G 87 14 926.5. However, in that device the grooves are incorporated in the furnace wall, as a result of which serious disadvantages arise, as has already been described. The type of shaping of the complimentary sides of the specimen support and grooves was derived from the above-mentioned petty patent and in this case serves for optimizing refinement of the invention.

When constructing tube furnaces and specimen supports, each person being skilled in the art must take account of usual tolerances which prevent disadvantageous effects of thermal expansion of the parts at the contacting positions.

Graphite tube furnaces according to the invention can be heated up by connection of electric terminals which engage essentially at the front part of the tube ends or by contact terminals applied laterally to the tube wall or by means of contact pieces material-lockingly connected to the tube wall, in a known manner. When heating through the wall surface it is to be noted that the contact pieces are not connected to third, fourth and fifth zones III, IV and V. When heating through the wall surface, for most usages a construction is advantageous in which the contact pieces connected laterally with the furnace wall are located in the plane of a longitudinal section guided parallel to the horizontal position of the specimen support.

The tube furnace and the specimen support are formed of any desired type of graphite, such as electrographite, pyrographite or vitreous carbon. Very pure graphite obtained from electrographite which is easily workable and only slightly contaminated by foreign elements, is preferred. Tube furnaces and supports are conveniently coated with a thin pyrographite layer which seals the graphite parts and improves their resistance to friction.

Graphite tube furnaces lined with pyrographite in accordance with the invention can also be used without specimen supports since the vaporization and atomization zone IV does not have any flutes and the flanges of the third and fifth zones III and V restrict outflow from one another to the atomization zone of the specimen fluid.

The invention provides a graphite tube furnace with a specimen support which has the following advantages or effects:

Setting of an optimized temperature profile with reference to the course of analysis with respect to time and with respect to the extent of the furnace chamber.

Possibility of matching the zones of the graphite tube furnace to the respective analytical and process technology situations.

Avoidance of undesired temperature sinks and large suppression of matrix effects.

Reliable immobilization of the specimen support against movement in any direction. As a result analysis can also be carried out in strong electric and magnetic alternating fields without disturbance.

Minimizing the mass of the specimen support while maintaining a machining cost that is usual for specimen supports according to the state of the art.

Economical reproducibility of the tube furnace by means of simple, essentially rotationally symmetrical shapes.

Usability of the structural principle of the graphite tube furnace for heating, as a matter of choice, from the tube ends or from the tube housing.

Other features which are considered as characteristic for the invention are set forth in the appended claims.

Although the invention is illustrated and described herein as embodied in a graphite tube furnace with a stationary specimen support for atomic absorption spectroscopy, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

FIG. 3A is a longitudinal-sectional view of a graphite tube furnace taken along the line III—III of FIG. 1 in the direction of the arrows, with specimen support pushed in;

FIG. 3B is a fragmentary, perspective view of a groove of a zone III with a specimen support pushed in;

Figure 1:
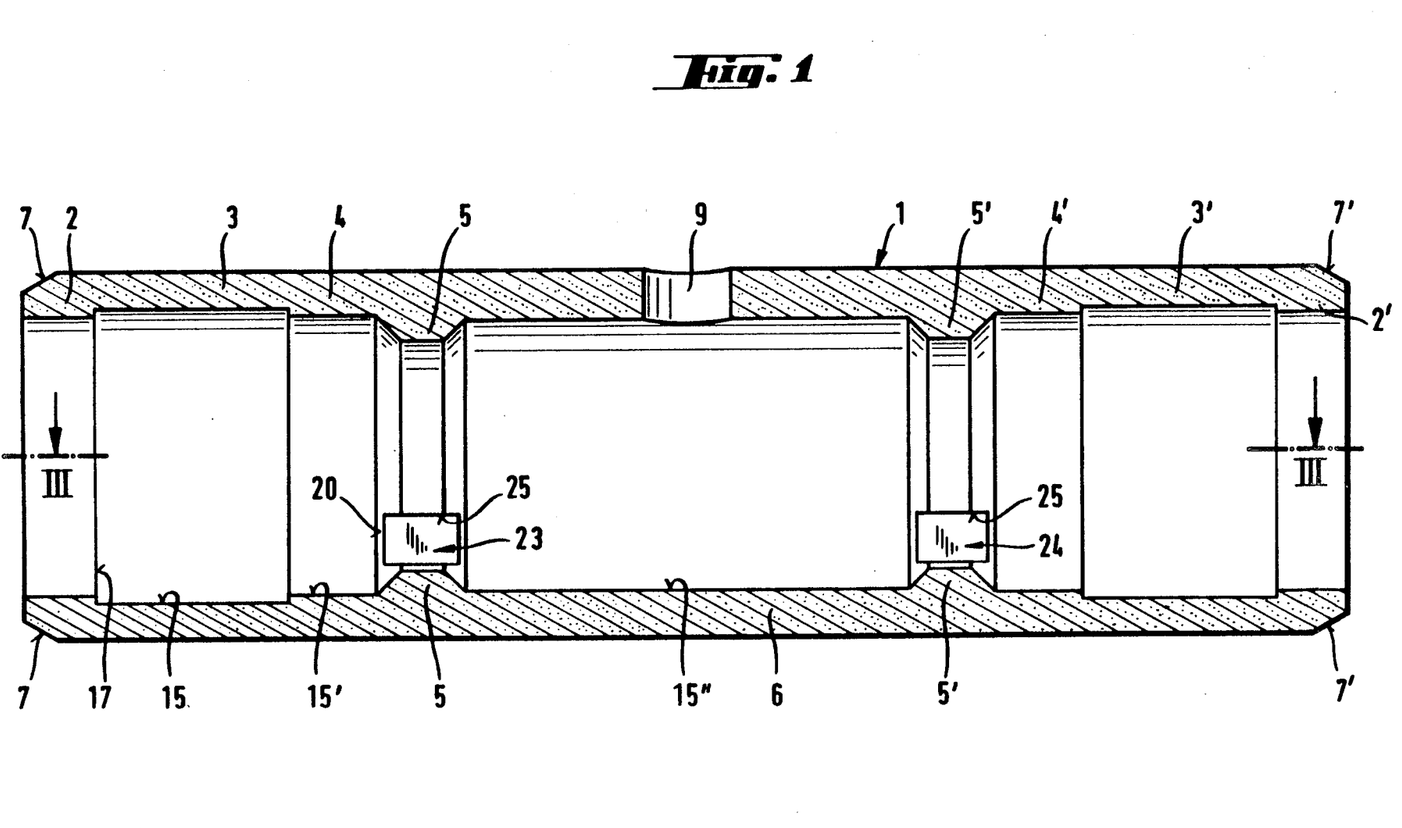
FIG. 1 is a diagrammatic, longitudinal-sectional view of a graphite tube furnace.

Referring now to the figures of the drawings in detail and first, particularly, to FIG. 1 thereof, there is seen a longitudinal-sectional view of a graphite tube furnace 1 according to the invention. As seen from the tube ends toward the interior, the following zones are present:

a first starting zone I bearing reference numeral 2, a seventh end zone VII with reference numeral 2', a second zone II with reference numeral 3 and a sixth zone VI with reference numeral 3' having reduced wall cross-sections, two zones 4, 4' optionally present between the second zone II with reference numeral 3 and a third zone III with reference numeral 5 as well as between the sixth zone VI with reference numeral 3' and a fifth zone V with reference numeral 5', wherein the third zone III with reference numeral 5 and the fifth zone V with reference numeral 5' are formed of surrounding flanges, and a fourth central zone IV with reference numeral 6 in which an analysis substance is vaporized and atomized.

The outsides of the zone I with reference numeral 2 and the zone VII with reference numeral 2' have conical surfaces 7, 7' for the connection of a non-illustrated electrical contacting configuration. The zone II with reference numeral 3 and the zone VI with reference numeral 3' serve for the prevention of heat sinks. The zones 4 and 4', which are in the form of intermediate zones, are introduced and disposed in such a way as to meet a requirement that they match the tube furnace to special requirements of the analysis configuration.

Disposed in the zones 5 and 5', which are in the form of surrounding flanges, are incorporated trapezoidal grooves 23, 24 which are opposite and in the same plane as one another. A specimen is pushed into the grooves. The central zone IV bearing reference numeral 6 is provided with an opening 9 for the introduction of an analysis substance.

Figures 2A, 2B, 2C:
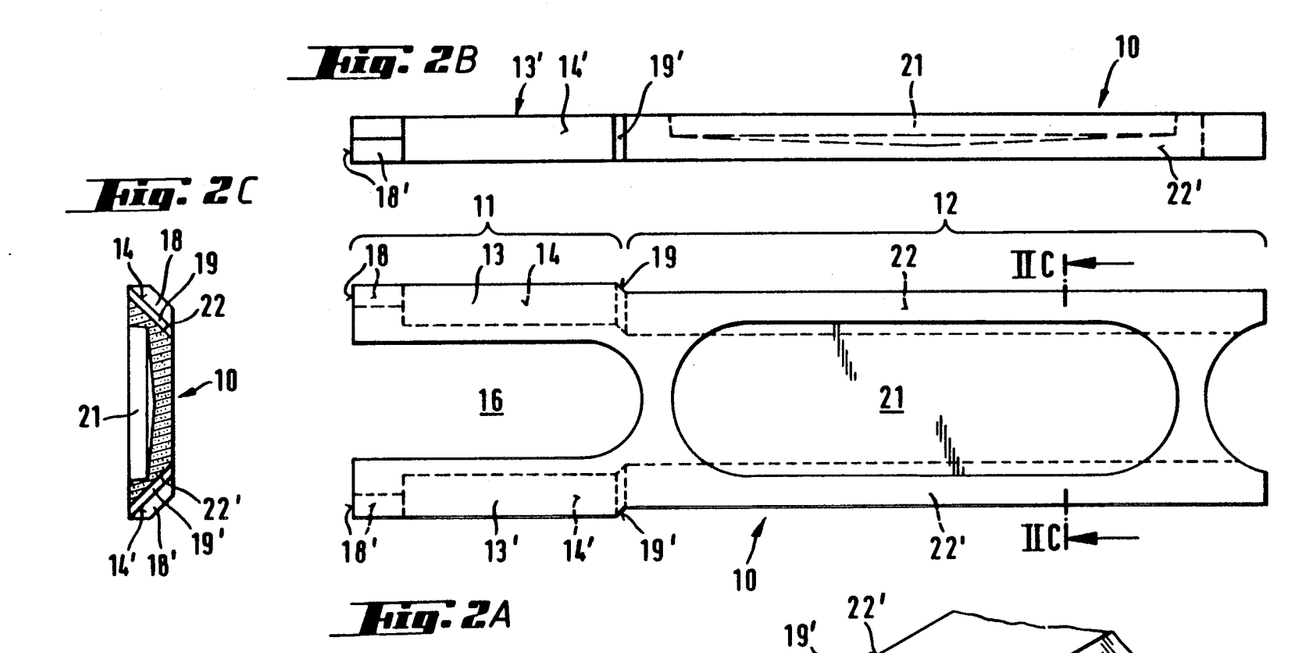
FIG. 2A is a top-plan view of a specimen support.
FIG. 2B is a side-elevational view of a specimen support.
FIG. 2C is a cross-sectional view of a specimen support taken along the line IIc—IIc of FIG. 2A, in the direction of the arrows.
Figure 2D:
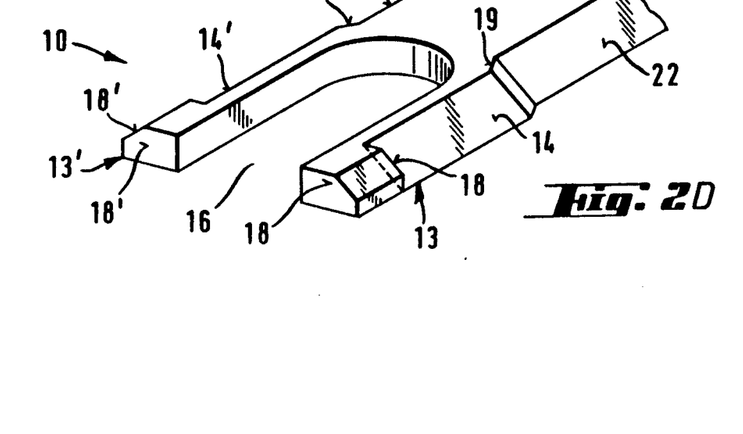
FIG. 2D is a fragmentary, perspective view of the lower surface of the specimen support as seen laterally from the front.
Figure 4A:
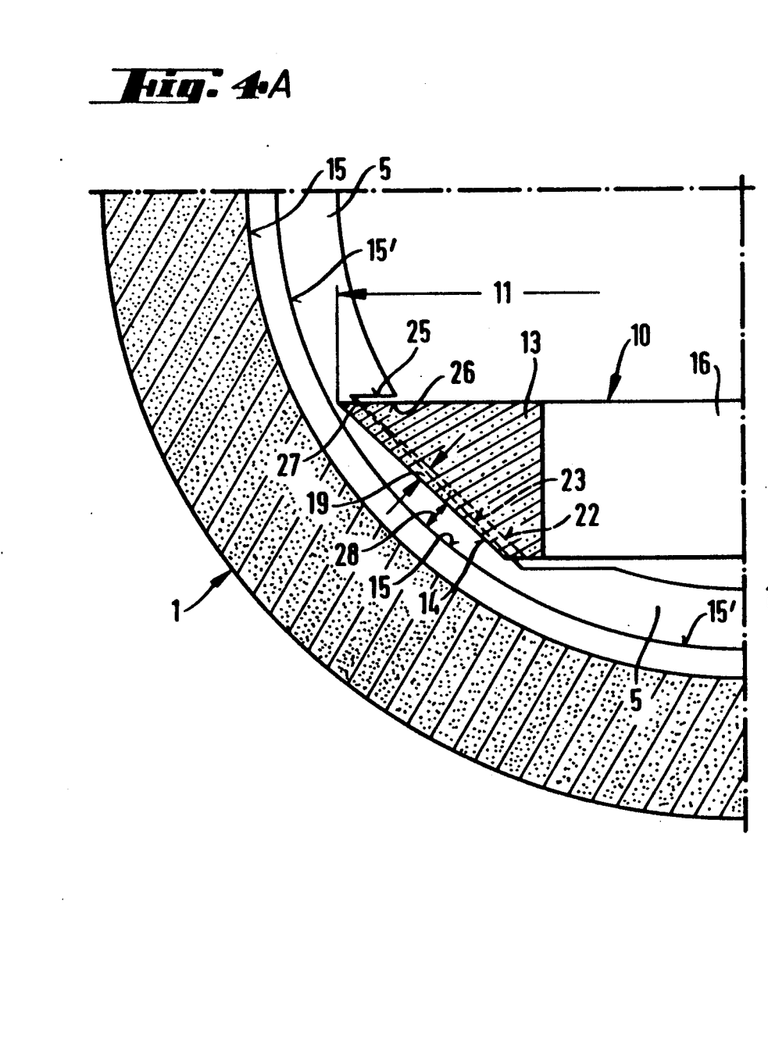
FIG. 4A is a fragmentary, enlarged, cross-sectional view of the graphite tube furnace, with a specimen support laid therein, at a zone II.

A specimen support 10 seen in FIGS. 2A to 2C is formed of a wider part 11 and a narrower part 12. The wider part 11 is formed of two webs or legs 13, 13' which enclose a U-shaped recess 16 and which extend from the narrow part 12. The lower surfaces of the webs 13, 13' have bevels 14, 14' in order to permit the webs 13, 13' to be kept apart from a tube furnace wall 15, 15' by a distance 28, as seen in FIG. 4A. The lower part of the two ends of both webs 13, 13' have cantilevers 18, 18' for maintaining the specimen support 10 stationary at an inner section 17 of the zone I bearing reference numeral 2. Two sections 19, 19' at a transition from the wider part 11 to the narrower part 12 of the specimen support 10 serve as an abutment at outer lateral edges 20 of the surrounding flange of the zone III with reference numeral 5 and hold the specimen support 10 against movement in the interior of the tube furnace. The narrower part 12 of the specimen support 10 has a trough-like, flat pan 21 on which the analysis substance is applied. Two outer, long sides of the part 12 are provided with bevels 22, 22', for holding the part 12 at a distance 29 from a furnace wall 15" at the central zone IV having reference numeral 6, as seen in FIG. 4B.

Figures 3A, 3B:
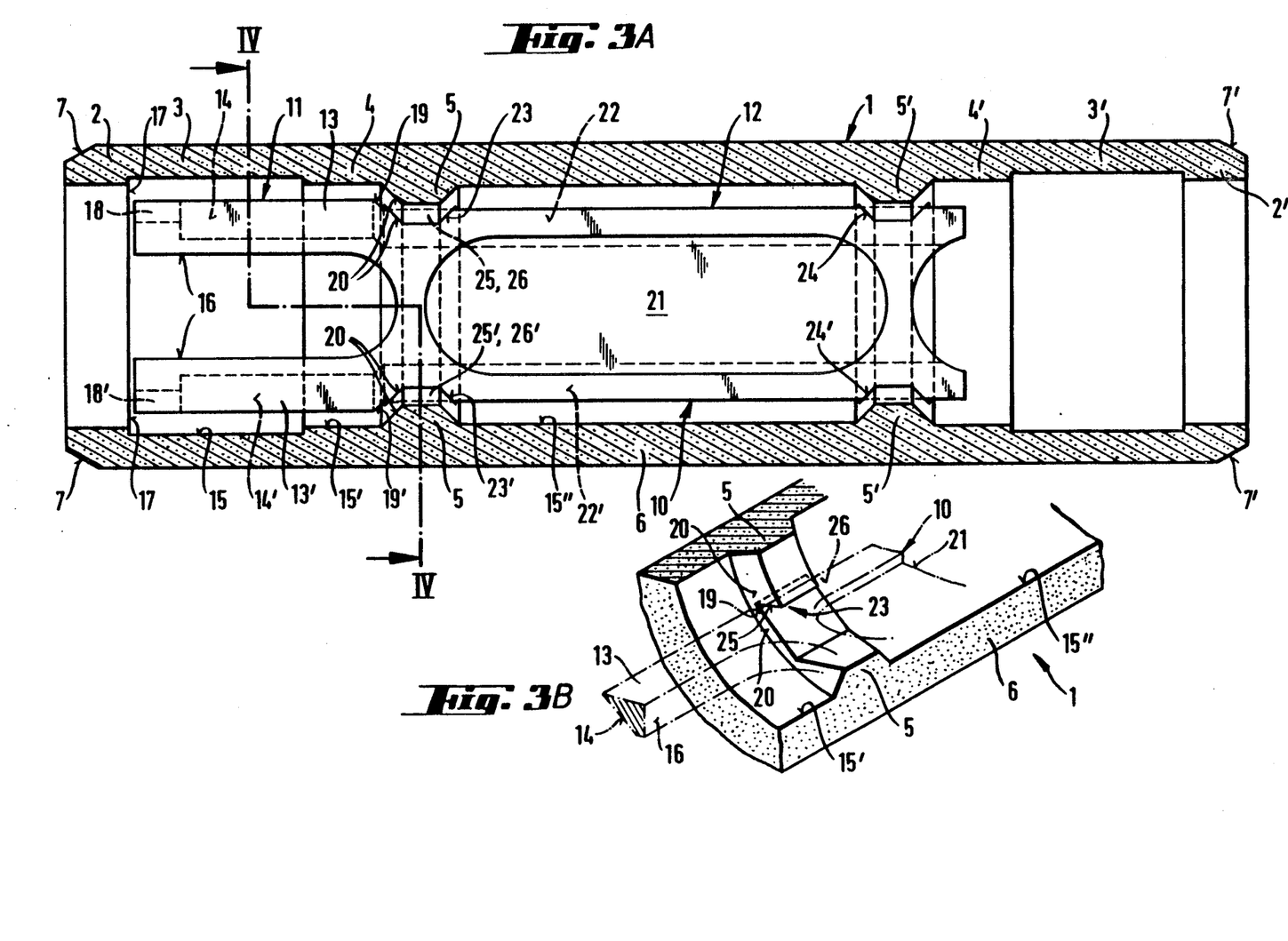

FIGS. 3A and 3B as well as 4A and 4B also illustrate and give the position of the specimen support 10 in the graphite tube furnace 1 and show that the specimen support 10 rests in the grooves or groove-shaped recesses 23, 23' 24, 24' in the flanges 5 and 5'; that the cantilevers 18, 18' of the wider part 11 of the specimen support 10 stand in alignment as abutments with the inner section 17 of the zone I having reference numeral 2; and that a securing of the longitudinal movement of the specimen support 10 in the other direction is effected as a result of the abutment of the sections 19, 19 at the transition from the wider 11 to the narrower 12 part of the specimen support 10 with the outer lateral edges 20 of the surrounding flange 5 of the zone III bearing reference numeral 5.

Figure 4B:
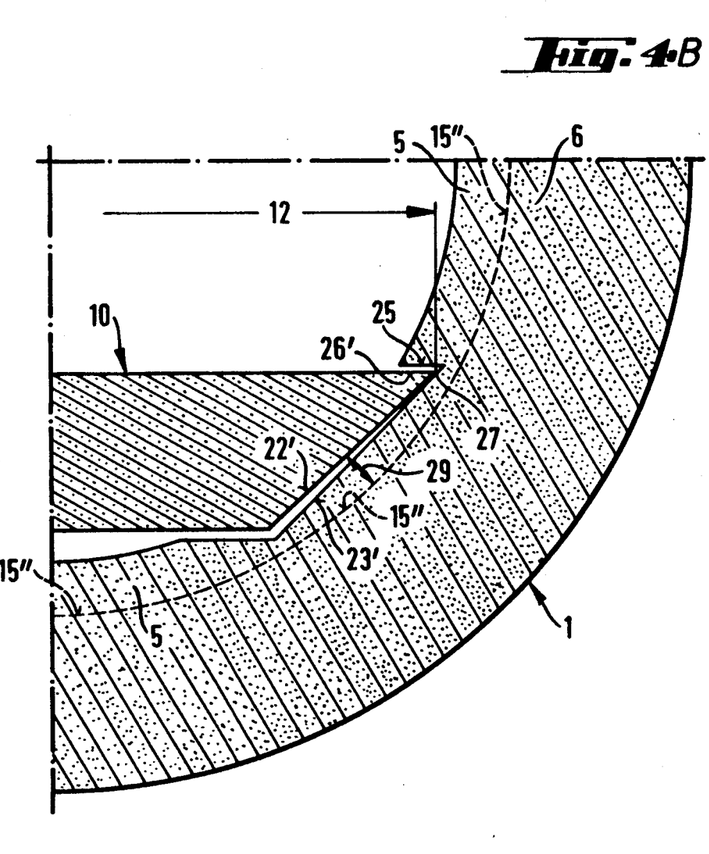
FIG. 4B is a view of the graphite tube furnace which is similar to FIG. 4A, with specimen support introduced therein, in the middle of the zone III.

The securing of the specimen support 10 against vertical movements in the grooves or groove-shaped recesses 23, 23', 24, 24' in the flanges 5 and 5' is shown especially clearly by FIG. 4B, which is an example of a cross-section through the graphite tube furnace with the specimen support 10 pushed in, in the middle of the surrounding flange of the zone III with reference numeral 5. Upper horizontal surfaces 25, 25' of the grooves 23, 23' overlap upper corner edges or zones 26, 26' of the specimen support 10 and secure them against vertical movements. The grooves 23, 23' amount to complimentary trapezoidal sections, as seen in cross-section. The specimen support 10 is likewise trapezoidally shaped. The surfaces 25 and 26 do not make contact with each other, so that a contact by means of which electric current or heat can flow, only exists along a contacting line 27. The specimen support 10 is so wide at its upper surface in relation to the depth of the grooves 23, 23', that the upper horizontal surfaces 25, 25' of these grooves safely cover the upper corner edges 26, 26' of the specimen support, even while providing a clearance necessary for compensation of the thermal expansion of tube furnace and the specimen support.

Figure 5:
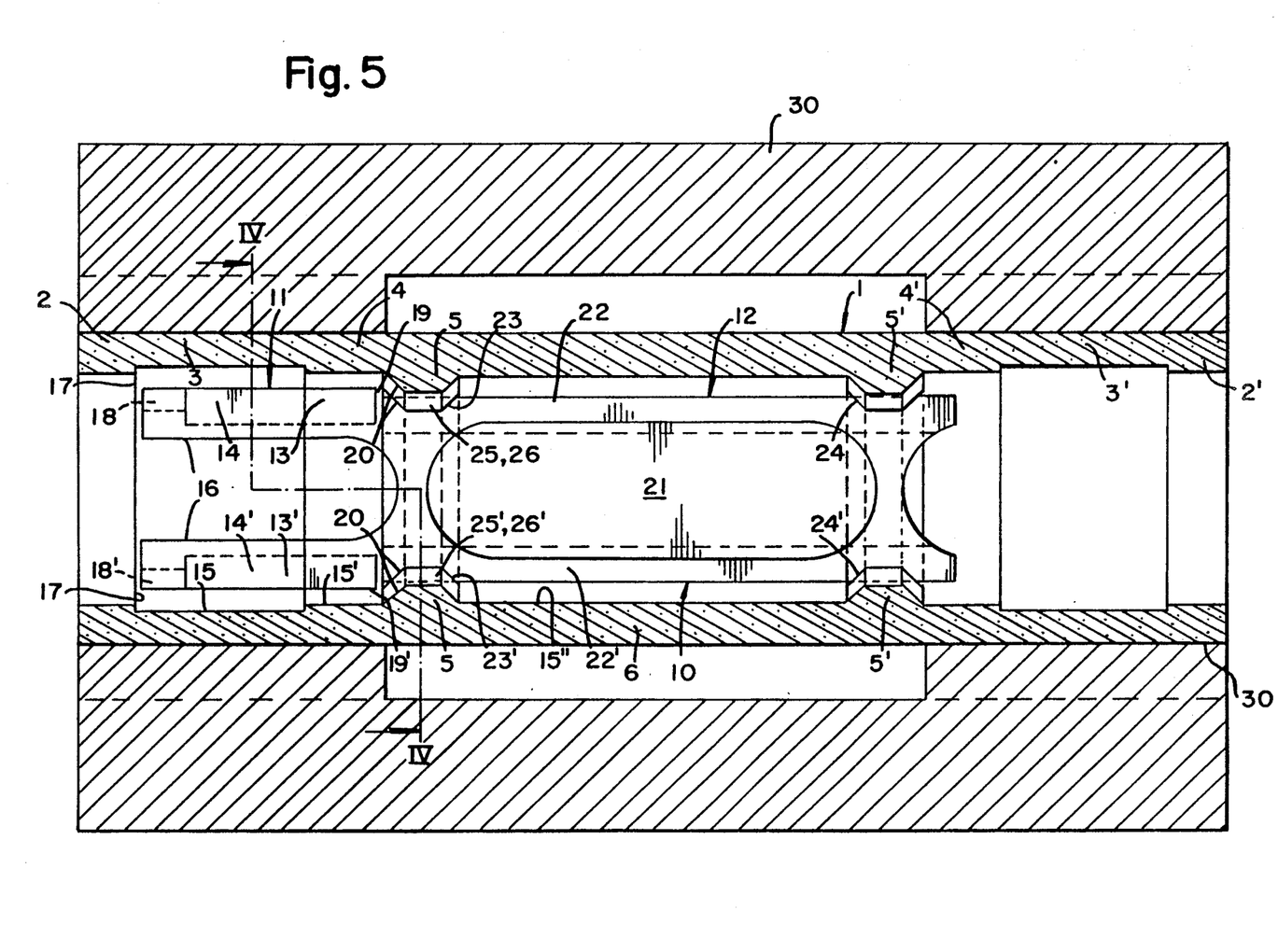
FIG. 5 is a view similar to FIG. 3a in which conical surfaces have been omitted but contact pieces have been added.

FIG. 5 is a view which is similar to FIG. 3A but shows contact pieces 30 laterally applied to the wall of the tube furnace for heating the tube furnace.

We claim:

1. A graphite tube furnace assembly for atomic absorption spectroscopy, comprising:

A) a graphite tube furnace having a longitudinal axis, an opening, ends, a wall with an inner surface, and an interior with a central region, said interior of said tube furnace having the following sequentially disposed zones as seen from one of said ends:
   1) a first starting zone with a first inner diameter and an inner section,
   2) a second zone with a second inner diameter being larger than said first inner diameter,
   3) a third zone with a third inner diameter being smaller than said first inner diameter, said third zone having a lateral edge facing said second zone and a surrounding flange formed at a distance from said ends along a circumferential line on said inner surface, said surrounding flange having a groove-shaped support formed therein,
   4) a fourth zone forming said central region and having a fourth inner diameter being greater than said third inner diameter and less than said first inner diameter,
   5) a fifth zone having a fifth inner diameter corresponding to said third inner diameter and another surrounding flange formed at a distance from said ends along a circumferential line on said inner surface, said other surrounding flange having another groove-shaped support formed therein,
   6) a sixth zone having a sixth inner diameter corresponding to said second inner diameter, and
   7) a seventh zone having a seventh inner diameter corresponding to said first inner diameter; and B) a specimen support to be inserted in said tube furnace and held in said groove-shaped supports at a distance from said inner surface,
   1) said specimen support having at least one relatively wider end section facing one of said ends of said tube furnace and at least one relatively narrower section adjoining said at least one wider end section and being disposed in said central region, after insertion of said specimen support in said tube furnace, said at least one wider end section having a shape cooperating with said inner section of said first starting zone and said lateral edge of said third zone of said tube furnace for preventing said specimen support from moving parallel to the longitudinal axis of said tube furnace after insertion of said specimen support into said groove-shaped supports, said sections having at least one recess formed therein for receiving an analysis specimen, and
   2) said specimen support having an end facing said opening of said tube furnace and being disposed at a distance from one of said ends of said tube furnace.

2. The graphite tube furnace assembly according to claim 1, wherein
   1) said groove-shaped supports in said flanges have trapezoidally-shaped cross-sections, and
   2) said specimen support has a part with a trapezoidally-shaped cross-section being disposed in said central region of said graphite tube furnace, said part securing said specimen support in place from below and above against outward movement after insertion of said specimen support in said groove-shaped supports, said trapezoidally-shaped cross-sections of said groove-shaped supports defining oppositely disposed surfaces of said flanges with different inclinations.

3. The graphite tube furnace assembly according to claim 1, wherein said at least one wider end section of said specimen support has two webs with a given resilience and ends with cantilevers facing said opening of said tube furnace, said webs being slightly bent through said first zone when pushing said specimen support into said furnace and springing back into a starting position after reaching said second zone, for preventing movements of said specimen support in the direction of said opening of said tube furnace by abutment against said inner section of said first zone.

4. The graphite tube furnace assembly according to claim 1, wherein said tube furnace is formed of two portions being divided along a cross-sectional surface at a vertical sectional plane passing through the center of said fourth zone, one of said portions including said first, second, third and half of said fourth zones and the other of said portions being a mirror image of said one portion.

5. The graphite tube furnace assembly according to claim 1, including means for heating said ends of said tube furnace.

6. The graphite tube furnace assembly according to claim 1, including means for heating said tube furnace through contact pieces laterally applied to said wall of said tube furnace.

7. The graphite tube furnace assembly according to claim 6, wherein said specimen support is disposed in a given horizontal position after insertion in said tube furnace, said wall of said tube furnace has an outer surface, said contact pieces are disposed at said outer surface in a plane of a longitudinal section parallel to said given horizontal position of said specimen support passing through the longitudinal axis of said tube furnace, and said contact pieces are not connected with said third, fourth and fifth zones of said tube furnace.

* * * * *